US007585272B2

(12) United States Patent
Abe (10) Patent No.: US 7,585,272 B2
(45) Date of Patent: Sep. 8, 2009

(54) ELECTRONIC ENDOSCOPE, AND METHOD FOR TRANSFERRING PROGRAMS

(75) Inventor: Kazunori Abe, Saitama (JP)

(73) Assignee: Fujinon Corporation, Saitama-shi (JP)

( * ) Notice: Subject to any disclaimer, the term of this patent is extended or adjusted under 35 U.S.C. 154(b) by 732 days.

(21) Appl. No.: 11/012,271

(22) Filed: Dec. 16, 2004

(65) Prior Publication Data

US 2005/0177023 A1 Aug. 11, 2005

(30) Foreign Application Priority Data

Dec. 26, 2003 (JP) .............................. 2003-433485

(51) Int. Cl.
*A61B 1/00* (2006.01)
*A61B 1/04* (2006.01)

(52) U.S. Cl. ...................... 600/101; 600/118; 600/134

(58) Field of Classification Search ................ 600/101, 600/109, 118, 160, 110, 134
See application file for complete search history.

(56) References Cited

U.S. PATENT DOCUMENTS

| | | | |
|---|---|---|---|
| 6,322,496 B1 * | 11/2001 | Iida et al. ..................... 600/118 |
| 2001/0051762 A1 * | 12/2001 | Murata et al. ................ 600/118 |
| 2002/0101507 A1 * | 8/2002 | Saito et al. ..................... 348/65 |
| 2002/0183590 A1 * | 12/2002 | Ogawa .......................... 600/117 |
| 2003/0025789 A1 * | 2/2003 | Saito et al. ..................... 348/76 |
| 2003/0060681 A1 * | 3/2003 | Yokota ......................... 600/117 |
| 2004/0019255 A1 * | 1/2004 | Sakiyama .................... 600/175 |
| 2004/0034280 A1 * | 2/2004 | Privitera et al. ............. 600/170 |
| 2004/0054256 A1 * | 3/2004 | Ogawa ......................... 600/118 |

* cited by examiner

*Primary Examiner*—John P Leubecker
*Assistant Examiner*—Philip R Smith
(74) *Attorney, Agent, or Firm*—Oblon, Spivak, McClelland, Maier & Neustadt, P.C.

(57) ABSTRACT

An electronic endoscope system which is largely composed of a scope and a processor. The processor includes a primary or patient's circuit and a secondary circuit which are so connected as to be able to communicate with each other for data transmission in an electrically insulated state. The secondary circuit on the side of the processor includes first MPU and first rewritable ROM which is connected with the first MPU through a first bus, a PC card slot connected to said first bus. In addition to data of picture images captured by an image sensor device mounted on a fore distal end portion of an insertion tube of a scope, a PC card stores a firmware version-up program to be executed for updating a firmware in the first ROM as soon as PC card is booted, starting from an address described in MBR of PC card. An update program of the firmware version-up program is transferred to and written into the first ROM at a high speed depending upon a clock speed of the first bus.

15 Claims, 8 Drawing Sheets

| FAT VALUE | MEANING |
|---|---|
| 0000h | UNUSED CLUSTER |
| 0001h | UNUSABLE CLUSTER |
| 0002h~FFF6h | CLUSTER NUMBER TO BE CHAINED NEXT |
| FFF7h | DEFECTIVE CLUSTER |
| FFF8h~FFFFh | LAST CLUSTER OF FILE |

FIG. 4

| NUMBER OF BYTE | CONTENTS |
|---|---|
| 8byte | FILE NAME |
| 3byte | EXPANSION |
| 1byte | ATTRIBUTE |
| 10byte | RESERVATION |
| 2byte | TIME OF CREATION |
| 2byte | DATE OF CREATION |
| 2byte | LEADING CLUSTER ADDRESS |
| 4byte | FILE SIZE |

ELECTRONIC ENDOSCOPE, AND METHOD FOR TRANSFERRING PROGRAMS

BACKGROUND OF THE INVENTION

1. Field of the Art

This invention relates to an electronic endoscope system having a scope and a processor and a method for transferring programs, and more particularly to an electronic endoscope system which is operated under the control of an upgradable firmware and a method for transferring upgrading or updating programs.

2. Prior Art

Heretofore, electronic endoscopes have been widely in use for observation, imaging, examination or treatment of an intracavitary portion of interest by introducing an elongated narrow insertion tube into the intracavitary portion. An electronic endoscope is usually equipped with an elongated insertion tube which is generally called "scope", and has an image sensor device, for example, like CCD (Charge Coupled Device) incorporated into a fore distal end portion of the insertion tube along with an illumination means to take picture images of an intracavitary site of interest under illuminated conditions. Picture images of an intracavitary site under observation are processed by a processor which is connected to the scope, and displayed on a monitor screen and at the same time stored in an image storage for later use, for example, for diagnostic purposes. In this manner, an electronic endoscope is largely constituted by a scope and a processor.

In this connection, in step with recent technical advancements, image sensors like CCD have been markedly improved in the aspects of miniaturization and densification. For example, the number of pixels on a CCD has increased drastically within a short period of time, making it possible to take sharper and clearer picture images of an intracavitary site under observation by an endoscope. In some cases, new functions like focusing and zooming functions are added for closer observation of an intracavitary side of interest. In case a new CCD of advanced functions is developed within a short period of time, it becomes necessary to change functions by adding a mechanism or mechanisms which can cope with the new CCD. Further, in case a new peripheral unit is added to an electronic endoscope, it becomes necessary for the electronic endoscope to control the newly added peripheral unit. Therefore, in order to control a CCD which is added with a new processor or in order to control a new peripheral unit or units, a necessity arises from time to time for updating the version of a firmware which is stored in a ROM (Read Only Memory) provided in the scope or in the processor.

For updating a firmware stored in a ROM of the processor, it has been the general practice to send a service staff to a location of an electronic endoscope for replacement of a firmware ROM. Namely, when the electronic endoscope to be updated is not in clinical use, after opening a cover of the processor, a firmware ROM of a current version is removed from a wiring board and replaced by a ROM of a new version. However, once a processor cover is opened, it may become difficult to guarantee safety of the processor because of possible electrical leaks or other problem, giving rise to a necessity for re-verification of the processor. Safety of the processor has to be guaranteed in a reassured manner especially with respect to the electronic endoscope which is electrically connected with the processor and directly introduced into a body cavity of a patient. Generally, safety of a processor is not guaranteed once a screw of a processor cover is removed. Therefore, it is desirable not to open a processor cover at the time of updating a firmware ROM.

In an attempt to solve the problem as mentioned above, there has been proposed a method of updating a firmware in a ROM without opening a processor cover, as disclosed in Japanese Laid-Open Patent Application 2000-245681 (Patent Literature 1). According to the invention of the Patent Literature 1, a notebook PC is connected to a processor of an electronic endoscope through an RS-232 interface, and an updating program which is stored in the notebook PC is transferred to a firmware ROM of the processor for updating the firmware to a new version.

According to the invention disclosed in the Patent Literature 1 mentioned above, it is possible to update a firmware ROM of a processor to a new version. However, generally speaking, a transfer rate is relatively low in the case of a serial transfer by way of RS-232 interface. That is to say, there is a problem that a transfer of an update program by way of RS-232 interface takes considerably a long time. A long transfer time of an updated program could result in a detrimentally long delay of an endoscopic examination. It is usually the case that, due to spatial restrictions, only one processor is installed in an endoscopic examination room. Therefore, when it becomes necessary to use a new scope in an endoscopic examination after finishing an examination by the use of a current system, a firmware ROM in the processor in the endoscopic examination room has to be updated before starting an examination with the new scope. If transfer of an updated program take a long time, a patient has to wait for a long time before taking an examination by a new scope. Besides, in a case where a notebook PC is connected to a processor for updating a firmware to a new version, the use of a non-medical notebook PC in a medical environment can give rise to other problems. In addition, to make things complicate, there has to be provided a cable for connecting the notebook PC to the processor as well as a power cable for connecting the notebook PC to a power source.

Provided internally of the processor are a patient's circuit mounting component parts which can be contacted with a living body, and a secondary circuit which operates on power supply from a commercial power source. A firmware ROM is provided in each one of the patient's circuit and the secondary circuit. In addition, another firmware ROM is provided in a scope connector which connects the patient's circuit with the scope. In a case where a firmware ROM is provided in this manner at a plural number of locations, it is usually the case that an updating program which is acquired by the secondary circuit is transferred to the patient's circuit by a communication means and then to the scope connector via the patient's circuit, instead of a firmware in each ROM independently of each other. In such a case, if it takes an unduly long time in acquiring an updating program at the secondary circuit by serial transfer prior to transfer to the patient's circuit and the scope connector, the serial transfer becomes a bottle neck requiring an extremely long time for updating the version of the firmware ROM in the patient's circuit as well as the firmware ROM in the scope connector.

In order to solve the problem of this sort, it is conceivable to transfer a firmware updating program from a flexible disk or CD-ROM drive which is connected to a USB (Universal Serial Bus) port, instead of transferring same from a notebook PC. However, in order to transfer a firmware updating program from a flexible disk or a CD-ROM which is connected to a USB port with only a slave controller, it is necessary to provide a master controller on the side of an electronic endoscope to control the slave controller, along with a program for driving and controlling a flexible disk or a CD-ROM which is connected to a USB port. In addition, it is impractical to use USB because it requires an immense memory space due to a large overhead.

SUMMARY OF THE INVENTION

With the foregoing situations in view, it is an object of the present invention to makes it possible to update, at a high speed and in a facilitated manner, a plural number of firmware ROMs which are incorporated into patient's circuit, secondary circuit and scope connector of an electronic endoscope, by the use of a PC card storing firmware version-up programs in addition to data of endoscopically captured picture images for which a PC card is usually resorted to as a storage. The firmware ROMs can be updated to a new version smoothly without causing detrimental delays to endoscopic examinations.

According to the present invention, in order to achieve the above-stated objective, there is provided an electronic endoscope system including a scope and a processor, which processor having a primary or patient's circuit and a secondary circuit so connected as to be communicable with each other for data transmission in an electrically insulated state, the electronic endoscope comprising: a first MPU provided in the secondary circuit on the side of the processor; a first writable ROM connected with the first MPU by way of a first bus; a PC card removably docked in a PC card slot connected to the first bus, for recording endoscopic picture images captured by an image sensor provided at a fore distal end portion of an insertion tube of the scope; a first firmware version-up program stored in the PC card to start from an address described in MBR of the PC card for updating a firmware in the first ROM; the first firmware version-up program being executed as soon as the PC card is started, and an update program in the first firmware version-up program being transferred from the PC card and written into the first ROM at a high speed depending upon a clock speed of the first bus.

In updating the firmware ROM to a new version, an update program, an update program is directly written into the firmware ROM from PC card by way of the first bus. That is to say, the update program can be read out from PC card at a high speed.

For updating a second firmware ROM in the patient's circuit to a new version, the patient's circuit comprises: a second MPU so connected as to be communicable with the first MPU in the secondary circuit; a second rewritable ROM connected with the second MPU by way of a second bus; and a second firmware version-up program stored in the PC card to start from an address described in MBR of the PC card for updating a firmware in the second ROM; as soon as the PC card is started, the first MPU reading in the second firmware version-up program at a highspeed depending upon a clock speed of the first bus, and transferring the second firmware version-up program of the second ROM to the second MPU to let the latter execute the second firmware version-up program to update a firmware in the second ROM to a new version.

For updating a third firmware ROM on a scope connector which connects the scope with the processor, the scope connector comprises: a third MPU so connected as to be able to be communicable with the first MPU in the secondary circuit; a third rewritable ROM connected with the third MPU by way of a third bus; a third firmware version-up program stored in the PC card to start from an address described in MBR of the PC card for updating a firmware in the third ROM; as soon as the PC card is started, the first MPU reading in the third firmware version-up program at a high speed depending upon a clock speed of the first bus, and transferring the third firmware version-up program of the third ROM to the third MPU to let the latter execute the third firmware version-up program to update a firmware in the third ROM to a new version.

The PC card can be connected to a computer other than the electronic endoscope system to utilize the data of endoscopic picture images which are stored in the PC card.

Further, according to the present invention, a plural number of MPU may be connected to the above-mentioned first bus.

Furthermore, a plural number of MPUs, ROMs and buses may be connected to the secondary circuit or the patient's circuit of the processor or to the scope connector if necessary.

In a preferred embodiment which will be described hereinafter, CDS, A/D converter and DSP are provided in the patient's circuit, and picture memory and D/A converter are provided in the secondary circuit, with an isolation between DSP and the picture memory. However, the present invention is not limited to this particular circuit arrangement. For example, DSP may be provided in the secondary circuit.

According to the present invention, arrangements are made to permit communications between the first MPU and the second MPU and between the second MPU and the third MPU for data transfer in packet mode. In this regard, different arrangements may be employed as long as data transmission is feasible between the respective MPUs.

Further, in a particular embodiment shown, a firmware version-up program is transferred from the first MPU to the third MPU via the second MPU. However, if desired, the version-up program may be transferred directly from the first MPU to the third MPU. That is to say, the version-up program may be transferred directly from the first MPU in the secondary circuit to the third MPU on the scope connector, instead of transferring the program by way of the second MPU in the patient's circuit.

The above and other objects and features of the present invention will become apparent from the following particular description of the invention, taken in conjunction with the accompanying drawings which show by way of example a preferred embodiment of the invention. Needless to say, the present invention should not construed as being limited to particular forms shown in the drawings.

DESCRIPTION OF PREFERRED EMBODIMENTS

Figure 1:
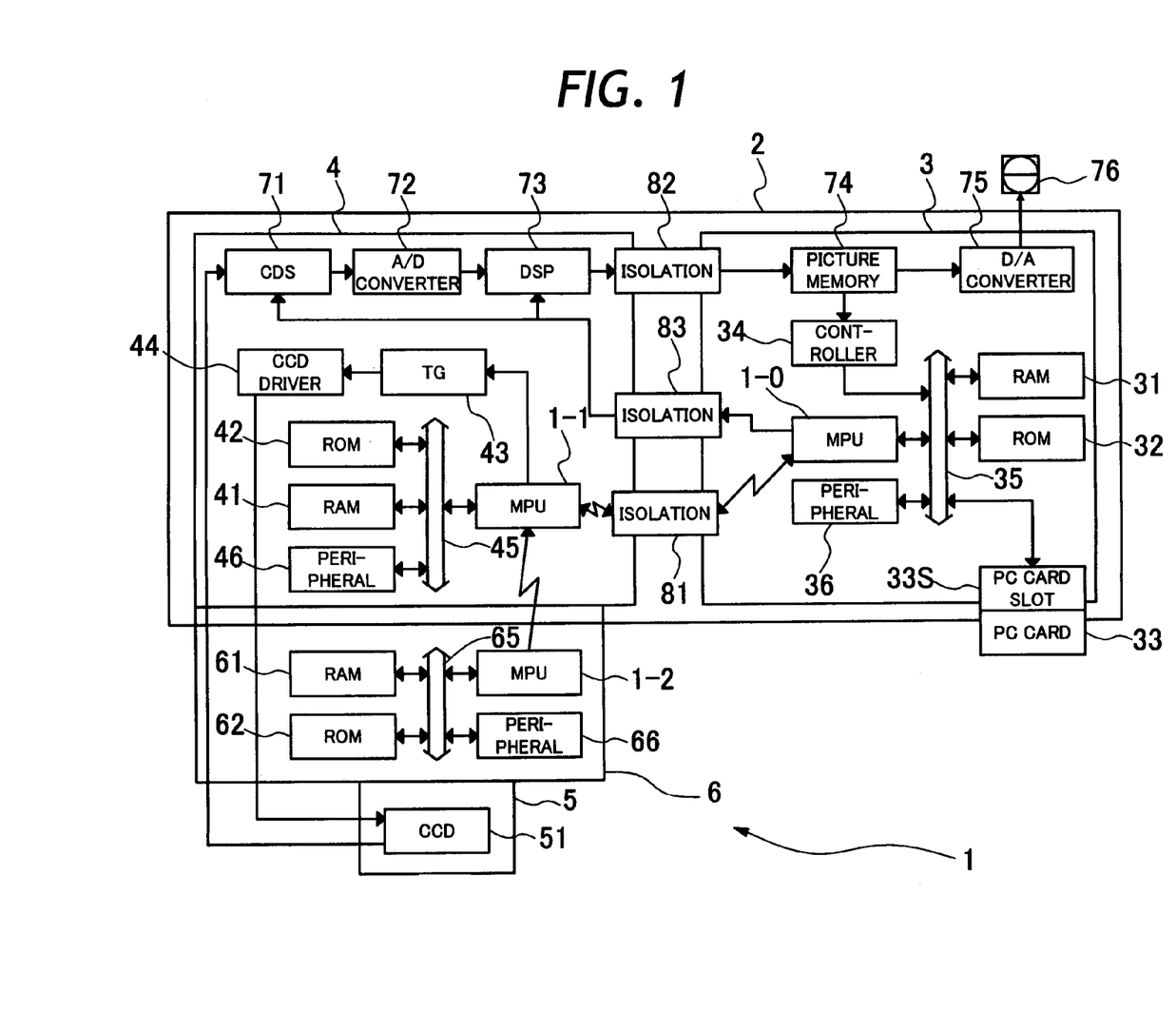
FIG. 1 is a circuit diagram showing circuit arrangements of an electronic endoscope system according to the present invention.

A. Configuration of Electronic Endoscope System According to the Invention:

Shown diagrammatically in FIG. 1 is configuration of an electronic endoscope system 1 according to the present invention. As shown in FIG. 1, the electronic endoscope system 1 is composed of a processor 2 and a scope 5. The processor 2 is constituted by a secondary circuit 3 and a patient's circuit 4.

The scope 5 is constituted by a CCD 51, and connected with the patient's circuit 4 through a scope connector 6 which is normally provided at a proximal end of a universal cable from the scope 5. According to the present invention, a PC card 33 is disconnectibly connected to a PC card slot 33S which is provided in the secondary circuit 3 of the processor 2.

The secondary circuit 3 includes MPU (Micro Processing Unit) 1-0, RAM (Random Access Memory) 31, ROM 32, PC card slot 33S, controller 34, bus 35, peripheral unit 36, picture image memory 74 and D/A converter (Digital Analog Converter) 75. On the other hand, the patient's circuit 4 includes MPU 1-1, RAM 41, ROM 42, TG (Timing Generator) 43, CCD driver 44, bus 45, peripheral unit 46, CDS (Correlated Double Sampling) 71, A/D converter (Analog/Digital Converter) 72, and DSP (Digital Signal Processor) 73. Further, the scope connector 6 includes MPU 1-2, RAM 61m ROM 62 and peripheral unit 66. The secondary circuit 3 and the patient's circuit 4 are connected with each other through isolations 81 to 83.

The processor 2 is arranged to process signals of a picture image from the scope 5 into video signals to display the picture image on an output device, for example, on a monitor screen 76, and composed of the secondary circuit 3 and the patient's circuit 4. In the case of an electronic endoscopes in use in medical fields, for the purpose of protecting patients and operators from electric shocks as caused by leak current, the patient's circuit 4 which is brought into direct contact with a patient and operator is electrically insulated from the secondary circuit 3 which receives a power supply from a commercial power source. That is, relative to the secondary circuit 3, the patient's circuit 4 is arranged in a form which sufficiently fulfills criteria of pressure resistance and leakage current. Since the secondary circuit 3 and the patient's circuit 4 are electrically insulated from each other in this manner, signals are transmitted between these circuits through isolations 81, 82 and 83, i.e., insulation means like transformers or phtocouplers.

In the secondary circuit 3, MPU 1-0, RAM 31, ROM 32, PC card slot 33S, controller 34 and peripheral unit 36 are connected through the bus 35. MPU 1-0 executes a predetermined program using RAM 31 as a work area to control the operation of the peripheral unit 36 and the controller 34 which is connected to the picture memory 74. ROM 32 is a rewritable memory like EEPROM (Electric Erasable Programmable Read Only memory), and stores programs to be executed by MPU 1-0 along with various data which are needed for control purposes. PC card 33 is a memory device for recording a picture image of endoscopic observation which is recorded in the picture memory 74, and connected to the bus 35 by way of the PC card slot 33S. Further, in addition to a picture image of endoscopic observation, the PC card 33 stores a program for updating firmware ROMs on the secondary circuit 3, patient's circuit 4 and scope connector 6. Through isolation 81, information is transmitted between MPU 1-0 and MPU of the patient's circuit 4. Namely, information is transmitted between MPU 1-0 and MPU 1-1 in packet mode. In this instance, for example, the packet size may be 256 bites, 512 bites or 1024 bites or any other arbitrary size as long as the two micro processing units can handle. Further, through isolation 83, MPU 1-0 controls CDS 71 and DSP 73, which will be described hereinlater.

The PC card 33 is preferred to be a memory device which is small in size but large in memory capacity, for example, a memory card like CF (Compact Flash) card (a trademark for a product of SanDisk Corporation of the United States of America) or Smartmedia (a trademark for a product of Toshiba Corporation), or a small-size hard disk. A memory card or a hard disk of this sort is extremely small in size and therefore can be carried very easily. Further, a memory card or a hard disk of this sort is very little in power consumption and can receive power supply from the processor 2. This means that no power supply cable is required for a memory card or hard disk.

The PC card 33 is directly connected to the bus 35 by way of the PC card slot 33S, so that MPU 1-0 can make an access to PC card 33 at the same access speed to RAM 31. Namely, MPU 1-0 can access both PC card 33 and RAM 31 at the speed, which depends on the clock speed of the bus 35. Generally, the clock speed of a bus to which a MPU is directly connected is higher as compared with USB and other buses, MPU 1-0 can make an access to PC card 33 at a high speed. For example, updating of a firmware by the use of PC card 33 is 3000 times higher in speed as compared with the conventional updating through an RS-232C port, and 2 to 8 times higher in speed as compared with updating by way of USB. According to the present embodiment, programs for updating firmware ROM are stored in PC card 33 in which picture images of endoscopic observation are recorded.

In the patient's circuit 4, MPU 1-1, RAM 41, ROM 42 and peripheral unit 46 are connected with each other through the bus 45. MPU 1-1 controls the peripheral unit 46 and TG 43 as well. TG 43, the so-called timing generator, delivers various timing pulses to CCD driver 44 which drives and controls CCD 51. Further, in addition to MPU 1-0, MPU 1-1 is so connected as to be able to transmit information to and from MPU 1-2 on the scope connector 6, and data are transmitted in packet mode between MPU 1-0 and MPU 1-2.

The scope connector 6 is a connector which connects the scope 5 with the patient's circuit 4, and constituted by MPU 1-2, RAM 61, ROM 62, bus 65 and peripheral unit 66. MPU 1-2, RAM 61, ROM 62 and peripheral unit are connected with each other through the bus 65. MPU 1-2 is so connected as to be able to transmit information to and from MPU 1-1, transmitting data to and from MPU 1-1 in packet mode.

The scope 5 is provided with CCD 51 which is supplied with timing pulse signals from CCD driver 44 through the scope connector 6. Data of a picture image taken by CCD 51 are fed from CCD 51 to CDS 71 of the patient's circuit 4 through the scope connector 6. After removing unnecessary noises by correlative double sampling at CDS 71, the picture data are converted into digital data at A/D converter 72 and then inputted to DSP 73. At DSP 73, the digital data of a picture image of endoscopic observation received from A/D converter 72 are processed for color separation and gamma correction to produce color video signals, for example, NTSC (National TV Standard Committee) color video signals. Picture data processed at DPS 73 are sent to and recorded in the picture memory 74 of the secondary circuit 3 by way of isolation 82. The digital picture data recorded in the picture memory 74 are converted into analog data at D/A converter 75 and displayed on a monitor screen 76. In this instance, picture images taken by CCD 51 are continuous picture images which are displayed on the monitor screen 76 as a motion picture. In this connection, when it is desired to capture a picture image of an intracavitary site under endoscopic observation, a desired picture image can be acquired from the picture memory 74 by controlling the controller 34 from MPU 1-0, and the acquired picture image can be recorded on PC card 33. Further, MPU 1-0 of the secondary circuit 3 controls CDS 71 and CDS 73 through isolation 83.

B. Original or Primary Usage of PC Card 33:

The above-mentioned PC card 33 is an expansion card which is detachably connectable to the bus 35 through the PC card slot 33S. In the present embodiment of the invention, PC card 33 is used as a memory device of a relatively large capacity like a flash memory or hard disk. For each patient, a plural number of picture images of endoscopic observation are recorded on PC card 33, for example, for use in diagnosing a progress at an endoscopic observation site.

Generally, an operator takes pictures of an intracavitary site of interest by the use of the electronic endoscope 1, giving the patient diagnostic explanations of taken pictures in a dispensary or a room separate from the endoscopic examination room in which the electronic endoscope 1 is installed. In the case of the present embodiment, data of picture images of an endoscopic observation site, taken by the electronic endoscope 1, are recorded on PC card 33, which is later on 1 connected to a computer in a dispensary or to a computer which needs data of picture images to display picture images stored on PC card 33. Since PC card 33 is relatively large in memory capacity, a large number of picture data can be stored in one PC card 33. In a case where one PC card 33 is allotted to each patient, it is possible to store on one PC card 33 the whole picture data of endoscopic examinations the patient has taken in the past. It follows that picture data in PC card 33 are useful in diagnosing progresses or changes at an endoscopic observation site in relation with a time axis over a certain period of time.

Figure 3:
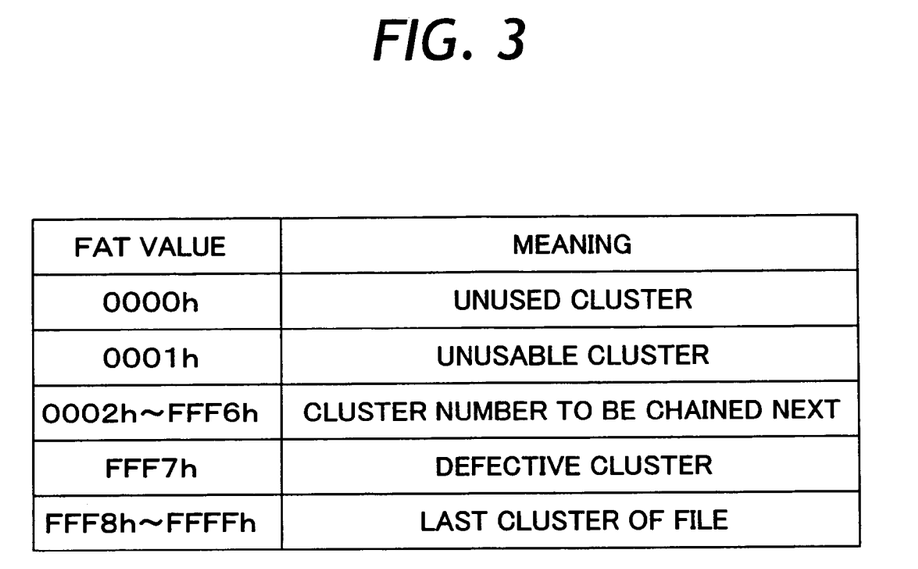
FIG. 3 is a chart of FAT structure.
Figure 4:
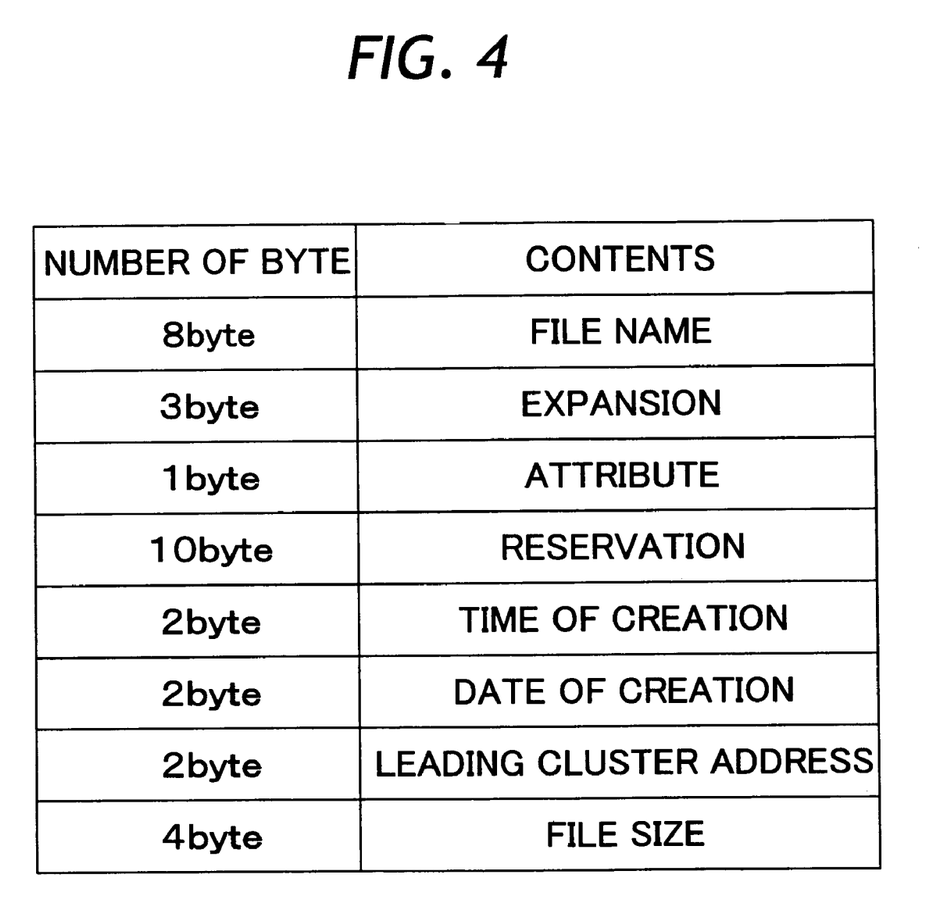
FIG. 4 is a chart of directory entry.

C. Memory Structure of PC Card 33 in Present Embodiment:

PC card 33 employed in the present embodiment has a memory structure which is arranged as described below with reference to FIGS. 2 to 4.

Figure 2:
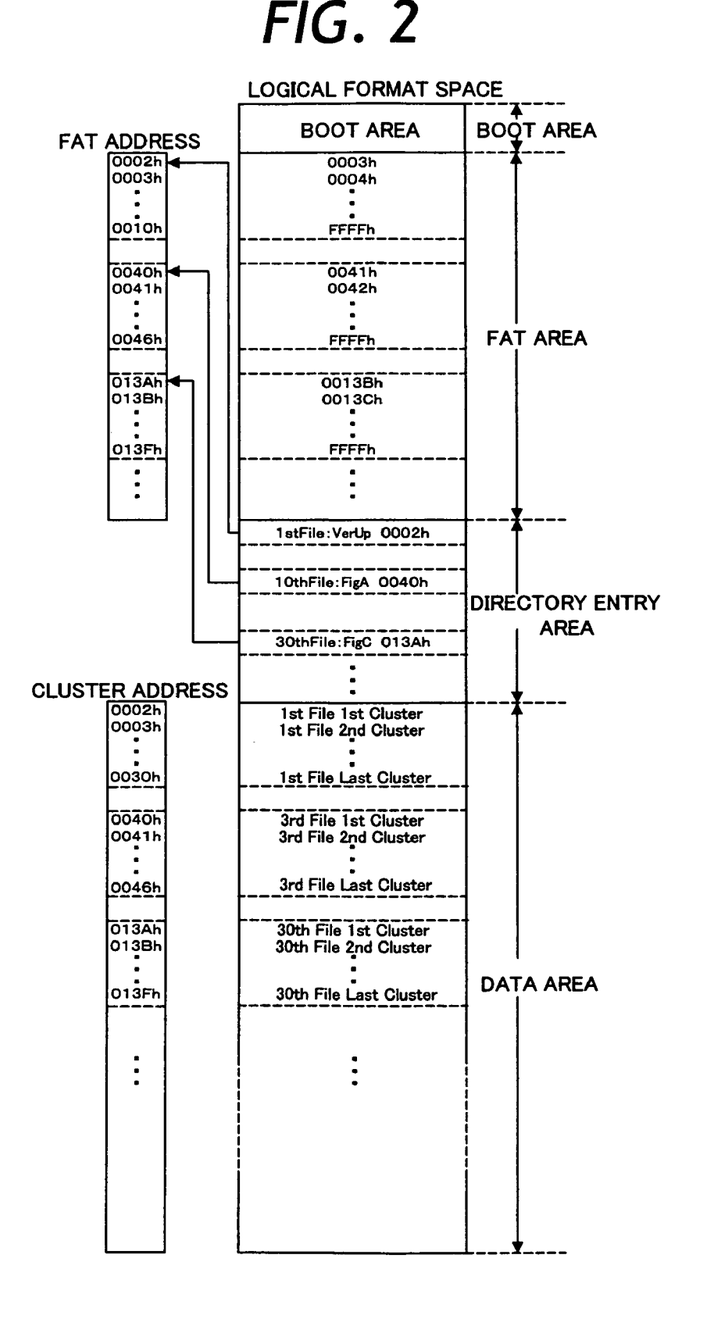
FIG. 2 is a chart of a logical format space of a PC card 33.

Shown in FIG. 2 is a structure of a logical format space of PC card 33 employed in the present embodiment. As seen in FIG. 2, the logical format space of PC card 33 is arranged in the order of cluster addresses, i.e., in the order of Boot Area, FAT (File Allocation Table) Area, Directory Entry Area and Data Area.

In this instance, PC card 33 makes an access to data by way of a cluster unit each constituted by a plural number of sectors. For example, in a case where a plural number of clusters are allotted to a file which contains data of picture images of endoscopic observation or an updating or version-up program of a firmware, an access is made to TAB cluster by cluster at the time of data read-out or write-in operation to acquire corresponding addresses on PC card 33.

MBR (Master Boot Record) and other information necessary for staring PC card 33 are stored in the boot area at a leading area of PC card 33. As shown in FIG. 3, FAT area contains a table of information with regard to cluster chains of each file, unused clusters and defective clusters. Also as shown in FIG. 3, Directory Entry Area stores the name of each file along with a file size and an address of a leading one of clusters of the file. Data Area stores data of picture images of endoscopic observation and actual data of programs as well. In the case of the particular embodiment shown, cluster addresses are expressed by 4-digit hexadecimal notation.

In order to make an access to an arbitrary one of clusters which are recorded on PC card 33, an address of a leading cluster is read out from Directory Entry Area, and then addresses of ensuing clusters are followed up with reference to FAT area to make an access to an aimed file. For example, in order to read out data of endoscopic observation picture images which is indicated as "FIG. A" in FIG. 2, a leading cluster address "0040h" of "FIG. A" is read out from Directory Entry Area, and an access to an aimed file is made by tracing the chain information for "0040h" in FAT. In the present embodiment, for the sake of convenience of explanation, a data file is shown as being constituted by a group of clusters of consecutive addresses. However, actually a data file is constituted by clusters of non-consecutive addresses. For example, in the case of the data file "FIG. A" with a leading cluster at the address of "0040h", a next cluster can be allotted with a non-consecutive address of "078Bh". Even if a data file is constituted by a number of clusters with non-consecutive addresses, an access can be made to that file by tracing the chain information in FAT.

According to the present embodiment, firmware ROMs on the electronic endoscope are updated by version-up programs as follows. Version-up programs for updating firmware ROMs in the secondary circuit 3, patient's circuit 4 and scope connector 6 are recorded on PC card 33.

As soon as PC card 33 is started to read in MBR, a program which is generally referred to as "a boot loader" is called and executed. In the case of the present embodiment, the boot loader is a version-up program. Namely, upon starting PC card 33, a version-up program is automatically started from an address which is described in MBR. Therefore, it suffices for MBR to contain a description of a top address of the version-up program, which can be stored in any place in the data area of PC card 33.

In the present embodiment, the version-up program includes a first version-up program for updating a firmware in ROM 32 to which PC card 33 is connected via PC card slot 33S and bus 35, a second version-up program for updating a firmware in ROM 42 in the patient's circuit 4, and a third version-up program for updating a firmware in ROM 62 on the scope connector 6.

C-1 Contents of $1^{st}$ Version-Up Program

Figure 5:
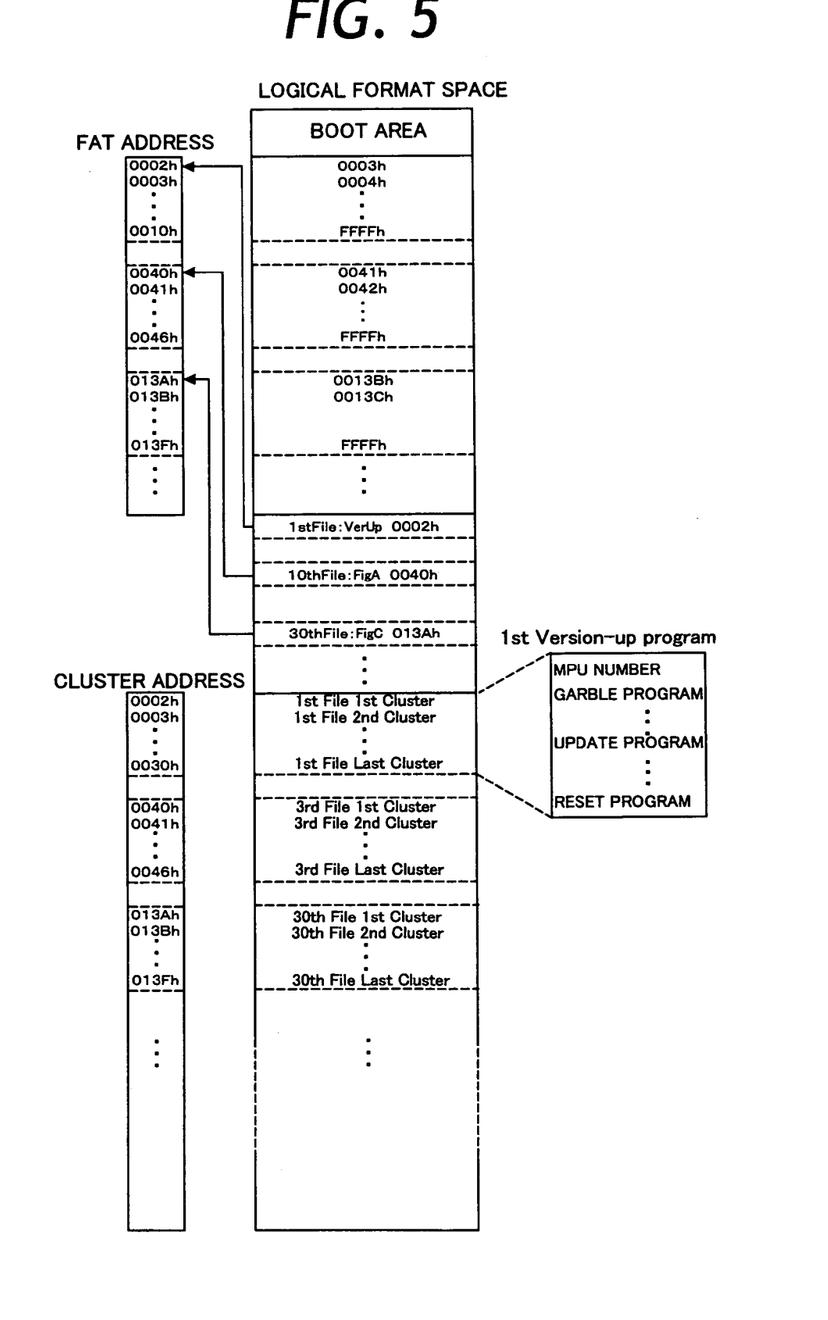
FIG. 5 is a chart of a first updating program.

Shown in FIG. 5 is the structure of the first version-up program. As shown, the first version is composed of MPU number, garble program, update program and reset program. MPU number indicates the number of MPU which is at the control of a firmware ROM to be updated. In the case of the present embodiment, if a last digit in an MPU number (i.e., a figure after a hyphen) is "0", it indicates that an MPU which is connected to the bus 35 is at the control. If a last digit in an MPU number is "1", it indicate that MPU in the patient's circuit 4 is at the control. If a last digit in an MPU number is "2", it indicates that MPU on the scope connector 6 is at the control. In the case of the circuitry arrangements shown FIG. 1, MPU 1-0 alone is connected to the bus 35. However, a plural number of MPUs can be connected to the bus 35. In such a case, second and third MPUs are labeled with numbers such as MPU 2-0 and MPU 3-0. The garble program a program for updating a firmware to a new version. Namely, by execution of the garble program, a new version of firmware is written into ROM 32. The update program is a main body of a program to be written into ROM 32, and, by writing in the update program, the firmware in ROM 32 is updated to a new version which, for example, copes with newly added functions. The reset program is a program for resetting RAM 31 and MPU 1-0 after the update program has been written into ROM 32. The reset program is the last program to be executed for updating the version of the firmware, and, when executed, the version-up procedure comes to an end. In this case, MPU number which is stored in the version-up program is "1-0".

C-2 Contents of $2^{nd}$ Version-up Program

Figure 6:
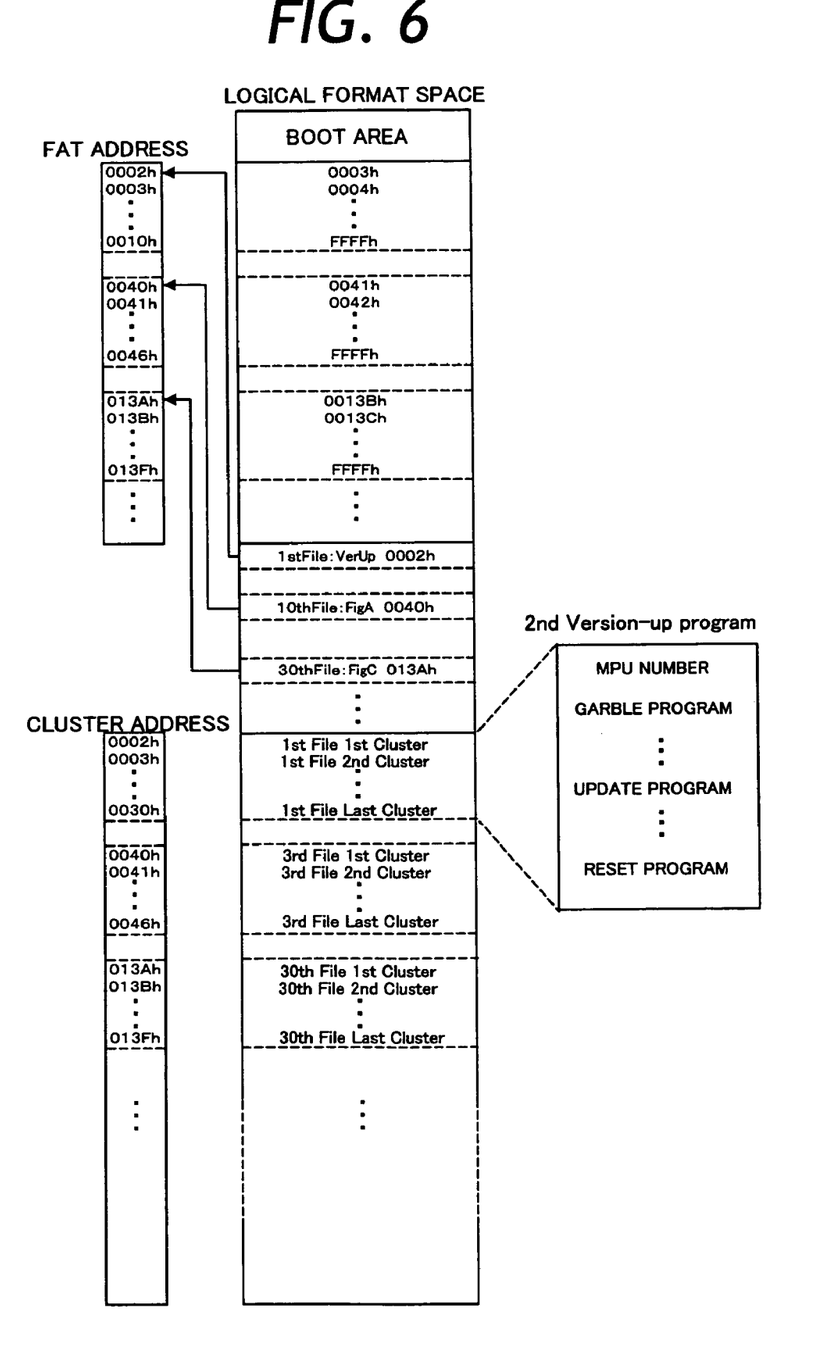
FIG. 6 is a chart of second and third updating programs.

Shown in 6 are contents of second and third update programs. As shown in FIG. 6, the second update program is composed of MPU number, garble program, update program and reset program. In the case of the particular embodiment shown, since ROM 42 is not connected to the bus 35 to which PC card 33 is connected through the PC card slot 33S, the garble program, update program and reset program which are necessary for updating the firmware in ROM 42 have to be transferred from MPU 1-0 to MPU 1-1. In the present embodiment, MPU 1-0 is communicable with MPU 1-1 through isolation 81, so that the garble program, update program and reset program are transferred from MPU 1-0 to MPU 1-1 by packet mode. In this case, MPU number which is stored in the second version-up program is "1-1".

C-3 Contents of $3^{rd}$ Version-up Program

The third version-up program is a program for updating a firmware in ROM 62 on the scope connector 6 to a new version, and composed of substantially the same components as the second version-up program described above. However, the third version-up program differs from the second version-up program in that the firmware version-up program including the garble program, update program and reset program are transferred from MPU 1-0 to MPU 1-2 via MPU 1-1.

As described above, according to the present embodiment, as soon as PC card 33 is booted, version-up programs which are recorded on PC card 33 are automatically executed one after another.

D. Actions

D-1 Actions of $1^{st}$ Version-up Program

Figure 7:
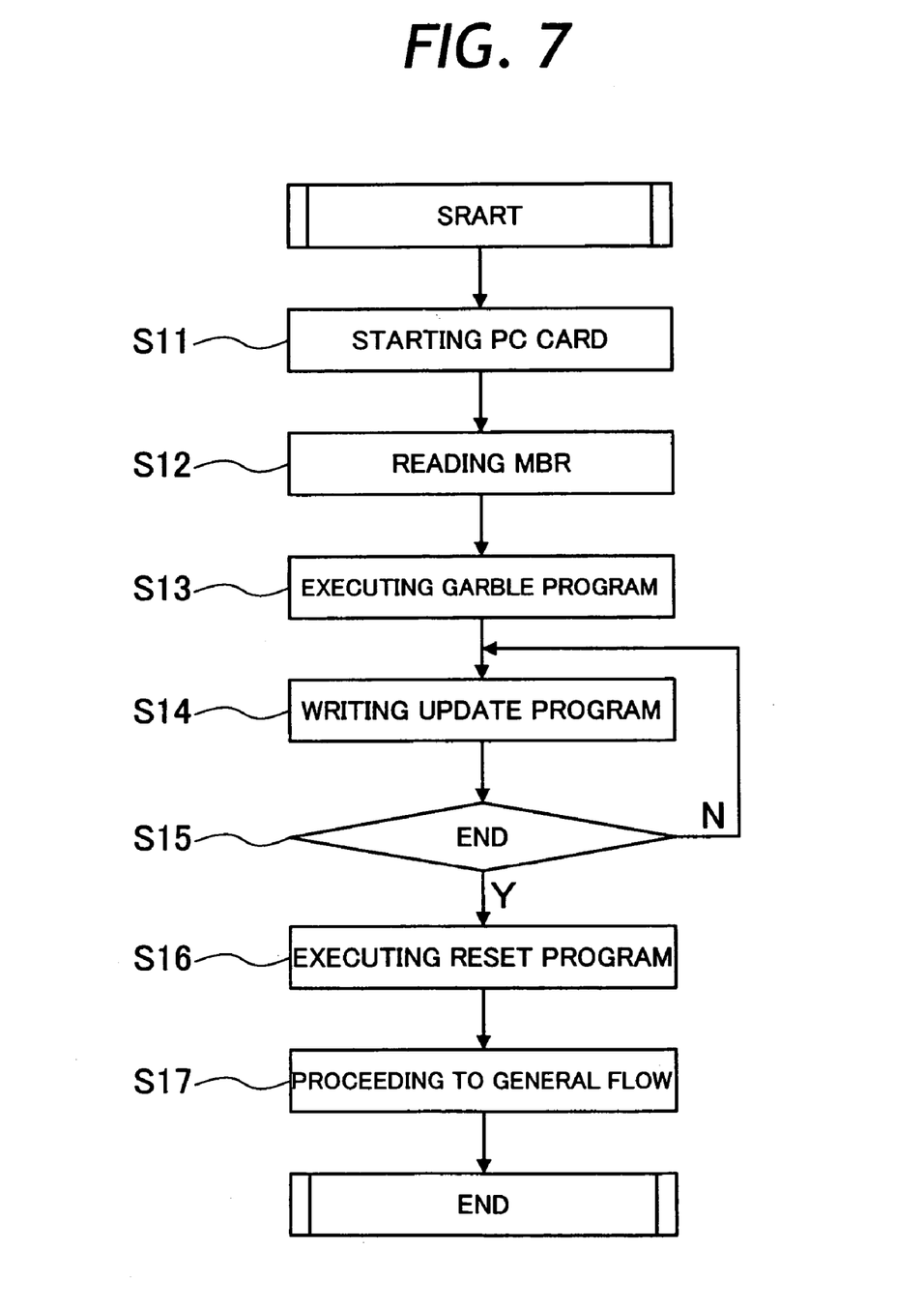
FIG. 7 is a flow chart of the first updating program.

PC card 33 which is connected to PC card slot 33S is started upon turning on power supply to the processor 2 (Step S11). Although in the present embodiment PC card 33 in PC card slot 33S is started upon turning on power supply of the processor 2, it can be started in a different way. For example, arrangements may be made such that PC card 33 is started by choosing same from a menu on a display means which is connected to the processor 2 along with an input means.

As soon as PC card 33 is started, MBR in a leading area of PC card 33 is read in (Step S12) to execute a version-up program from an address which is described in MBR. In executing the version-up program, MPU 1-0 recognizes from a file name M1_0_2_11 that this software is for MPU 1-0 and its version is 2.11. In the next place, MPU 1-0 acquires the version number of current ROM 32 and ascertain whether or not it is smaller than 2.11, that is, whether or not it is of an old version. If the current version is larger than 2.11, the operator is warned by way of a display device which is not shown, compelling to end the version-up or permitting rewriting upon entering an instruction through an input device which is not shown. On the other hand, if the number of current version is smaller than 2.11, that is to say, when the version-up program is found to be of a new version, the garble program is executed (Step S13). The garble program is a program which controls an operation of copying the update program to ROM 32. The garble program is executed by MPU 1-0 to copy the update program to ROM 32 (Step S14).

For updating a firmware, it has been the general practice to transfer an update program to RAM from an external storage like CD-ROM or flexible disk and then copy the update program in RAM to ROM. At the time of transferring a firmware update program from an external storage like CD-ROM or flexible disk, the update program can be copied to ROM only after it is once transferred to RAM which is used as a working area. In the case of the present embodiment of the invention, PC card 33 which is connected to the bus 35 can be accessed as a storage similar to RAM 31, and there is no need for providing a working area in updating a firmware because the update program on PC card 33 can be directly written into ROM 32. Namely, as the bus 35 is exclusively occupied by PC card 33 and ROM 32, the update program on PC card 33 can be written into ROM 32 at a high speed depending upon the clock speed of the bus 35, making it possible to update a firmware to a new version at a high speed.

Upon completing writing of the update program from PC card 33 in ROM 32 (Step S15), the reset program is executed (Step 16) to end the version-up and proceed to a general flow (Step S17).

D-2 Actions of $2^{nd}$ Version-up Program

Actions of the second version-up program are described below with reference to FIGS. 1, 2, 6 and 8.

Figure 8:
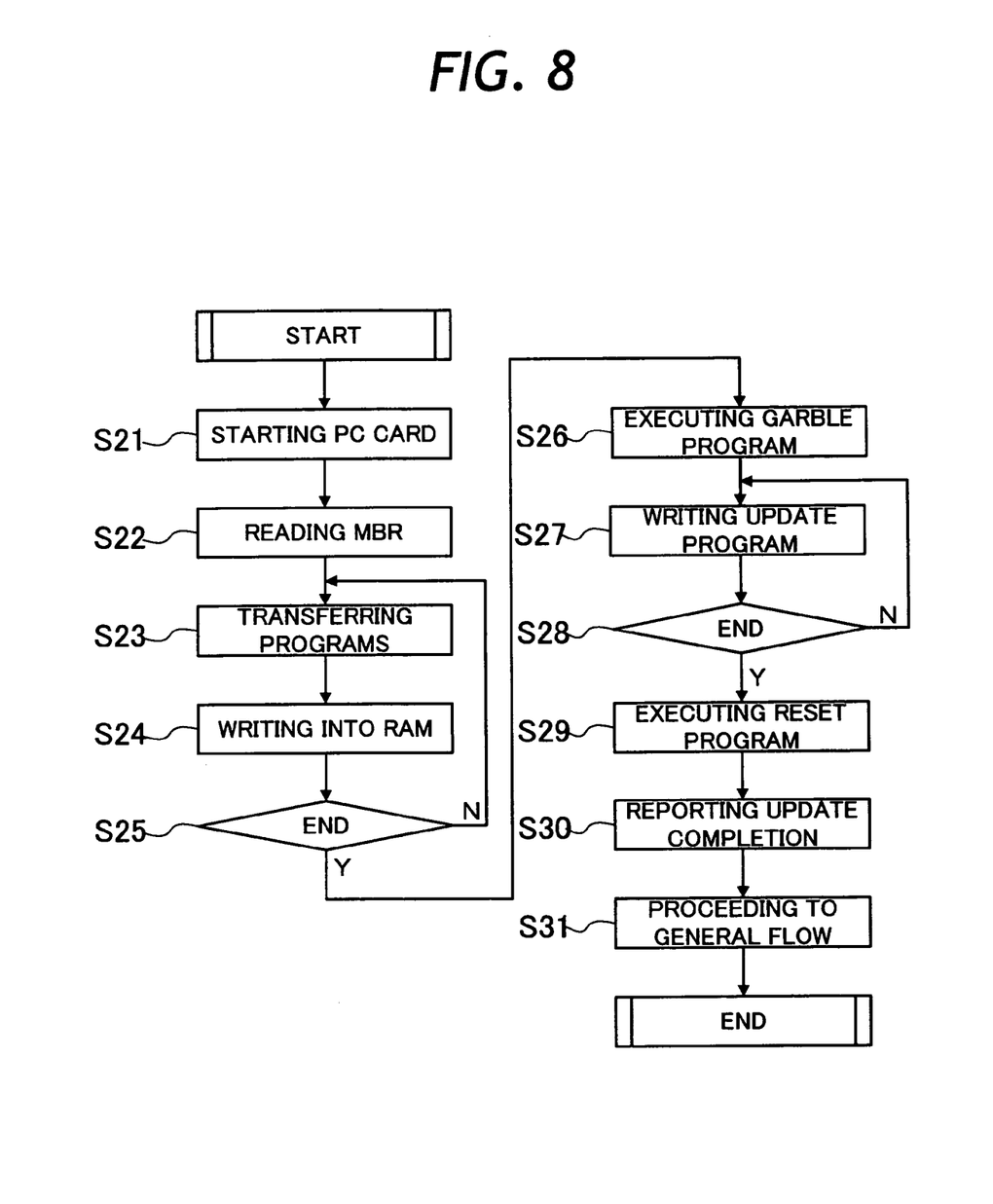
FIG. 8 is a flow chart of the second and third updating programs.

In the first place, similarly to the first version-up program, as soon as PC card 33 is started (Step S21), MBR is read in from a leading area of PC card 33 (Step S22), and the version-up program is executed from an address which is described in MBR. Upon starting execution of the version-up program, MPU 1-0 recognizes from a file name, which is described for example as M1_1$_{13}$ 2_11, that this program is for MPU 1-1 and the version of the software is 2.11. In the next place, MPU 1-0 acquires a current version of ROM 42 and make a judgment as to whether or not it is smaller than 2.11 (whether or not it is an old version). If the current version is larger than 2.11, a warning message is indicated on a display device which is not shown, compelling to end the version-up or permitting rewriting upon entering an instruction through an input device which is not shown. On the other hand, if smaller than 2.11, that is to say, in case the version-up program is found to be of a new version, MPU 1-0 transfers a garble program, update program and reset program to MPU 1-1 by packet mode via isolation 81 (Step S23). MPU 1-1 successively unwinds and develops received packets to write in RAM 41 (Step S24). Upon completing writing in RAM 41 (Step S25), the garble program in RAM 41 is executed (Step S26). Namely, at this time point garble program, update program and rest program have been already written into RAM 41 by packet transfer from MPU 1-0, so that MPU 1-1 can execute the garble program in RAM 41. Similarly to the counterpart in the first version-up program, the garble program is a program for copying the update program to ROM 42 and executed by MPU 1-1 to write the update program into ROM 42 (Step S27). Upon completing writing-in of the update program (Step S28), MPU 1-1 execute the reset program in RAM 41 to rest MPU 1-1 and RAM 41 (Step S29). After execution of the reset program, MPU 1-1 reports completion of firmware version-up of ROM 42 to MPU 1-0 via isolation 81 (Step S30). MPU 1-0 which holds the MPU number "1-1" know that version-up is under way at MPU 1-1. Therefore, until a report of "updating complete" is received from MPU 1-1, MPU 1-0 takes no action, assuming that version-up of ROM 42 is still under way. Finally, at a time point when MPU 1-0 receives a report of "updating complete", it proceed to a general flow (Step S31).

D-3 Actions of $3^{rd}$ Version-up Program

Actions of the third version-up program are described below with reference to FIGS. 1, 2, 6 and 8.

In the first place, similarly to the first version-up program, as soon as PC card 33 is started (Step S21), MBR in a leading area of PC card 33 is read in (Step S22) to start a version-up program from an address which is described in MBR. Upon starting execution of the version-up program, MPU 1-0 recognizes from a file name, for example named M1_2_2_11, that this program is for MPU 1-2 and that the version of the software is 2.11. In the next place, MPU 1-0 acquires the current version of ROM 62, and makes a judgment as to whether or not it is smaller than 2.11 (whether or not it is an old version). If larger than 2.11, a warning message is indicated on a display device which is not shown, compelling to end the version-up or permitting rewriting upon entering an instruction through an input device which is not shown. On the other hand, if smaller than 2.11, that is to say, in case the version-up program is found to be of a new version, MPU 1-0 transfers garble program, update program and reset program to MPU 1-2 by packet mode via MPU 1-1 (Step S23). MPU 1-2 successively unwinds and develops received packets to write in RAM 61 (Step S24). As soon as all packets are transferred from MPU 1-0 to MPU 1-2 and written into RAM 61 (Step S25), the garble program in RAM 61 is executed (Step S26). Namely, at this time point the garble program, update program and reset program have already been written into RAM 61 by packet transfer from MPU 1-0, so that MPU 1-2 can execute the garble program in RAM 51 MPU 1-2. Similarly to the counterpart in the first version-up program, the garble program is a program for copying the update program to ROM 62 and executed by MPU 1-2 to write the update program into ROM 62 (Step S27). As soon as the update program is completely written into ROM 62 (Step S28, MPU 1-2 execute the reset program in RAM 61 to reset MPU 1-2 and RAM 61 (Step S29). After executing the reset program, MPU 1-2 sends an update report to MPU 1-0 via MPU 1-1 to the effect that the firmware of ROM 62 has been completed (Step S30). MPU 1-0 which holds the MPU number "1-2" know that MPU 1-2 has been at the task of version-up. Therefore, until a report "update complete" is received from MPU 1-2, MPU 1-0 takes no action assuming that version-up of the firmware of ROM 62 is still under way. At a time point when MPU 1-0 finally receives a report "update complete", it proceeds to a general flow (Step S30).

As described above, according to the present embodiment, a leading address of a firmware updating program is described in MBR of PC card 33 which is normally used for storing picture endoscopically captured images, so that a firmware version-up program can be executed from that address, reading in the firmware version-up program upon starting PC card 33. PC card 33, which is connected to the bus 35 through PC card slot 33S, can be accessed at the same speed as RAM 31, so that the firmware in ROM 32 can be updated to a new version at a high speed.

Further, since MPU 1-0 can access PC card 33 at a high speed, it can get version-up programs at a high speed. Therefore, MPU 1-0 cannot be a bottle neck in getting a version-up program from PC card 33 at the time of updating the firmware ROM 42 in the patient's circuit 4 which is electrically insulated from the secondary circuit 3 on the side of PC card 33 or at the time of updating the firmware ROM 62 on the scope connector. Accordingly, the firmware ROM 42 as well as firmware ROM 62 can be updated at a high speed.

Furthermore, PC card 33, which is in the form of a small memory card like CF card or SmartMedia or a small-size hard disk, can be easily in a convenient manner, in addition to the advantage that it is extremely small in power consumption and does not require an external power supply.

What is claimed is:

1. An electronic endoscope system including a scope and a processor, which processor having a primary or patient's circuit and a secondary circuit so connected as to permit communication and data transmission therebetween in an electrically insulated state, said electronic endoscope comprising:

a first MPU provided in said secondary circuit on the side of said processor;

a first writable ROM connected with said first MPU by way of a first bus;

a PC card removably docked in a PC card slot connected to said first bus, for recording endoscopic picture images captured by an image sensor provided at a fore distal end portion of an insertion tube of said scope;

a first firmware version-up program that includes a top address described in a master boot record (MBR) of said PC card to be read as soon as said PC card is booted, and upon booting said PC card, being automatically read from said top address being configured to update a firmware in said first ROM;

said first firmware version-up program being executed as soon as said PC card is activated by said MPU, an update program in said first firmware version-up program being transferred from said PC card and written into said first ROM at a high speed depending upon a clock speed of said first bus, and said patient's circuit includes a second MPU so connected as to be communicable with said first MPU in said secondary circuit;

a second rewritable ROM connected with said second MPU by way of a second bus; and a second firmware version-up program stored in said PC card to start from an address described in MBR of said PC card for updating a firmware in said second ROM, wherein as soon as said PC card is activated by said first MPU, said first MPU reading in said second firmware version-up program at a high speed depending upon a clock speed of said first bus, and transferring said second firmware version-up program of said second ROM to said second MPU to let the latter execute said second firmware version-up program to update a firmware in said second ROM to a new version, and said first MPU is configured to take no action until a report is received from said second MPU that updating of a firmware of said second ROM has been completed.

2. An electronic endoscope system as defined in claim 1, wherein said update program is directly written into said first ROM from said PC card via said first bus.

3. An electronic endoscope system as defined in claim 1, wherein one or more than one MPU is connected to said first bus in addition to said first MPU.

4. An electronic endoscope system as defined in claim 1, wherein said MPU is adapted to recognize a version number of said first firmware version-up program from a file name of the latter, and to execute said first firmware version-up program only when newer than a current version of a firmware in said first ROM.

5. An electronic endoscope as defined in claim 1, wherein said PC card is connectible to a computer other than said electronic endoscope system for the purpose of utilizing data of endoscopic picture images stored on said PC card.

6. An electronic endoscope system as defined in claim 1, wherein said patient's circuit is provided with said second MPU, said second ROM and said second bus in a plural number.

7. An electronic endoscope system as defined in claim 1, wherein said first MPU is configured to recognize a version number of said second firmware version-up program from a file name and to proceed to execution of said second firmware version-up program only when newer than a version number of a firmware currently stored in said second ROM.

8. An electronic endoscope system as defined in claim 1, wherein said PC card is connectible to a computer other than said electronic endoscope system for the purpose of utilizing data of endoscopic picture images stored on said PC card.

9. An electronic endoscope system as defined in claim 1, wherein a scope connector is configured to connect said scope with said processor comprises:

a third MPU so connected as to be able to be communicable with said first MPU in said secondary circuit;

a third rewritable ROM connected with said third MPU by way of a third bus;

a third firmware version-up program stored in said PC card to start from an address described in MBR of said PC card for updating a firmware in said third ROM;

as soon as said PC card is activated by said first MPU, said first MPU reading in said third firmware version-up program at a high speed depending upon a clock speed of said first bus, and transferring said third firmware version-up program of said third ROM to said third MPU to let the latter execute said third firmware version-up program to update a firmware in said third ROM to a new version.

10. An electronic endoscope system as defined in claim 9, wherein said third firmware version-up program is transferred from said first MPU to said third MPU via said second MPU.

11. An electronic endoscope system as defined in claim 9, wherein said firmware version-up program is directly transferred from said first MPU to said third MPU.

12. An electronic endoscope system as defined in claim 9, wherein said scope connector is provided with a plural number of said third MPU, said third ROM and said third bus in a plural number.

13. An electronic endoscope system as defined in claim 9, wherein said first MPU is configured to recognize a version number of said firmware version-up program from a file name and to proceed to execution of said second firmware version-up program only when newer than a version number of a firmware currently stored in said third ROM.

14. An electronic endoscope system as defined in claim 9, wherein said first MPU is configured to take no action until a report is received from said third MPU that updating of a firmware of said third ROM has been completed.

15. An electronic endoscope system as defined in claim 9, wherein said PC card is connectible to a computer other than said electronic endoscope system for the purpose of utilizing data of endoscopic picture images stored on said PC card.

* * * * *